United States Patent
Ito et al.

(10) Patent No.: US 8,920,378 B2
(45) Date of Patent: Dec. 30, 2014

(54) INDWELLING NEEDLE DEVICE

(75) Inventors: Toru Ito, Hiroshima (JP); Ryoji Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 63 days.

(21) Appl. No.: 13/698,481

(22) PCT Filed: Apr. 26, 2011

(86) PCT No.: PCT/JP2011/060168
§ 371 (c)(1), (2), (4) Date: Nov. 16, 2012

(87) PCT Pub. No.: WO2011/152160
PCT Pub. Date: Dec. 8, 2011

(65) Prior Publication Data
US 2013/0066276 A1 Mar. 14, 2013

(30) Foreign Application Priority Data
Jun. 4, 2010 (JP) ................. 2010-128778

(51) Int. Cl.
*A61M 5/178* (2006.01)
*A61M 25/06* (2006.01)
*A61M 5/158* (2006.01)

(52) U.S. Cl.
CPC ........... *A61M 5/158* (2013.01); *A61M 25/0631* (2013.01); *A61M 25/0606* (2013.01)
USPC .................................................. 604/167.06

(58) Field of Classification Search
CPC ............... A61M 25/0606; A61M 25/0693; A61M 25/0097; A61M 2025/0687; A61M 29/00; A61M 25/0612; A61M 25/0618; A61M 25/0631; A61M 2025/09125; A61M 25/0662; A61M 25/09

USPC .............. 604/164.01, 164.04, 164.07, 168.01
See application file for complete search history.

(56) References Cited

U.S. PATENT DOCUMENTS 4,722,725 A * 2/1988 Sawyer et al. ................... 604/27
5,279,572 A * 1/1994 Hokama ................... 604/168.01
(Continued)

FOREIGN PATENT DOCUMENTS

CN 201231004 5/2009
JP 48-026790 3/1973
(Continued)

*Primary Examiner* — Nicholas Lucchesi
*Assistant Examiner* — Diva K Chander
(74) *Attorney, Agent, or Firm* — Hamre, Schumann, Mueller & Larson, P.C.

(57) ABSTRACT

When a hub (40) is in an initial position at which it is located on the front end side of an inner cavity of a shield (20), an inner needle (50) penetrates an outer needle (30) and protrudes from a leading end of the outer needle to the outside, and when the hub is in a retracted position at which it is located on the rear end side of the inner cavity of the shield, the inner needle is housed within the inner cavity of the shield. A first side hole (31) is formed in an outer circumferential face of the outer needle, and a second side hole (51) is formed in an outer circumferential face of the inner needle. When the hub is in the initial position, an inner circumferential face of a region (33) of the outer needle that contains the first side hole is in close contact with the outer circumferential face of the inner needle, and the second side hole is located closer to the hub than the region where the inner circumferential face of the outer needle is in close contact with the outer circumferential face of the inner needle. Thus, a priming operation for filling a gap between the inner needle and the outer needle with blood can be easily performed, and leakage of blood through the side hole of the outer needle during puncture does not occur.

6 Claims, 10 Drawing Sheets

(56) References Cited

U.S. PATENT DOCUMENTS

| | | | |
|---|---|---|---|
| 6,352,521 B1* | 3/2002 | Prosl | 604/167.03 |
| 6,440,119 B1* | 8/2002 | Nakada et al. | 604/506 |
| 6,524,277 B1* | 2/2003 | Chang | 604/164.02 |
| 6,692,473 B2* | 2/2004 | St. Cyr et al. | 604/264 |
| 6,921,386 B2* | 7/2005 | Shue et al. | 604/164.01 |
| 7,722,567 B2* | 5/2010 | Tal | 604/164.01 |
| 7,833,201 B2* | 11/2010 | Carlyon et al. | 604/168.01 |
| 7,922,696 B2* | 4/2011 | Tal et al. | 604/165.01 |
| 8,192,402 B2* | 6/2012 | Anderson et al. | 604/164.1 |
| 8,192,404 B2* | 6/2012 | Murashita et al. | 604/167.01 |
| 8,398,598 B2* | 3/2013 | Carlyon et al. | 604/168.01 |
| 2004/0068232 A1* | 4/2004 | Hart et al. | 604/167.06 |
| 2005/0192535 A1* | 9/2005 | Takagi et al. | 604/164.08 |
| 2008/0039796 A1* | 2/2008 | Nakajima | 604/167.03 |
| 2009/0018511 A1* | 1/2009 | Fujii et al. | 604/195 |
| 2009/0082733 A1* | 3/2009 | Fujii | 604/164.08 |
| 2010/0179478 A1* | 7/2010 | Kobayashi et al. | 604/167.01 |

FOREIGN PATENT DOCUMENTS

| | | | |
|---|---|---|---|
| JP | 2006-297062 | | 11/2006 |
| JP | 2007125126 A | * | 5/2007 |
| JP | 2009-142492 | | 7/2009 |

* cited by examiner

INDWELLING NEEDLE DEVICE

TECHNICAL FIELD

The present invention relates to an indwelling needle device that includes a soft outer needle and a hard inner needle and is configured so that it is inserted into a patient in a state in which a leading end of the inner needle protrudes from a leading end of the outer needle and then the inner needle can be retracted from the outer needle.

BACKGROUND ART

Indwelling needle devices are widely used for treatment such as infusion, blood transfusion, and extracorporeal blood circulation. Leaving a metal needle inside a blood vessel may injure the blood vessel, and for this reason, Patent Document 1 discloses an indwelling needle device that includes a soft outer needle and a hard inner needle and is configured so that it is inserted into a blood vessel of the patient in a state in which the leading end of the inner needle protrudes from the leading end of the outer needle and then the inner needle can be retracted from the outer needle.

Figure 8A:
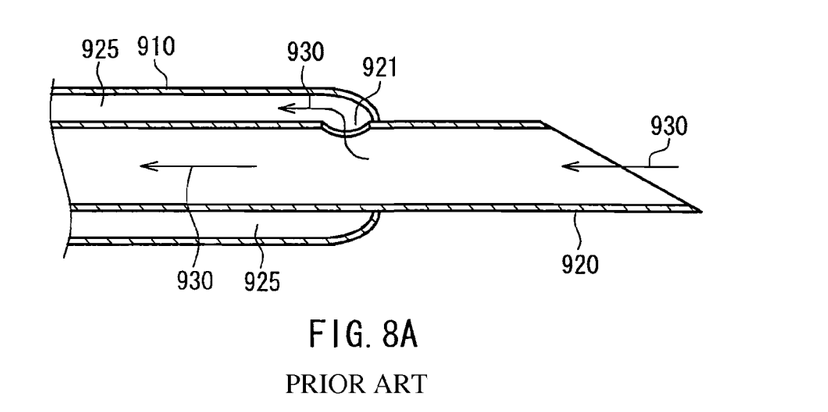
FIG. 8A is a cross-sectional view showing a leading end of an inner needle protruding from a leading end of an outer needle of a conventional indwelling needle device, and the vicinity thereof.

FIG. 8A is a cross-sectional view showing a leading end of an inner needle 920 protruding from a leading end of an outer needle 910 of the indwelling needle device disclosed in Patent Document 1 and the vicinity thereof. A side hole 921 is formed in an outer circumferential face of the inner needle 920. In the state shown in FIG. 8A, when the inner needle 920 and the outer needle 910 are sequentially inserted into a blood vessel of the patient, blood 930 of the patient flows inside the inner needle 920, and also passes through the side hole 921 of the inner needle 920 and flows inside a gap 925 between the inner needle 920 and the outer needle 910. When the outer needle 910 is composed of a transparent or translucent material, the blood flowing through the gap 925 can be visually observed, and flashback of the blood can be checked easily. Moreover, in addition to an inner cavity of the inner needle 920, the gap 925 can also be filled with the blood of the patient, so that in, for example, hemodialysis, a priming operation is facilitated, and the risk that blood in which air is mixed may be returned to the patient can be reduced.

CITATION LIST

Patent Document

Patent Document 1: JP 2006-297062A

DISCLOSURE OF INVENTION

Problem to be Solved by the Invention

In hemodialysis, when an opening at the leading end of a needle is brought into contact with an inner wall of a blood vessel, the blood flow rate decreases. Thus, in indwelling needle devices for use in hemodialysis, generally, a side hole is formed in an outer circumferential face of the needle in order to ensure a flow channel for blood.

Figure 8B:
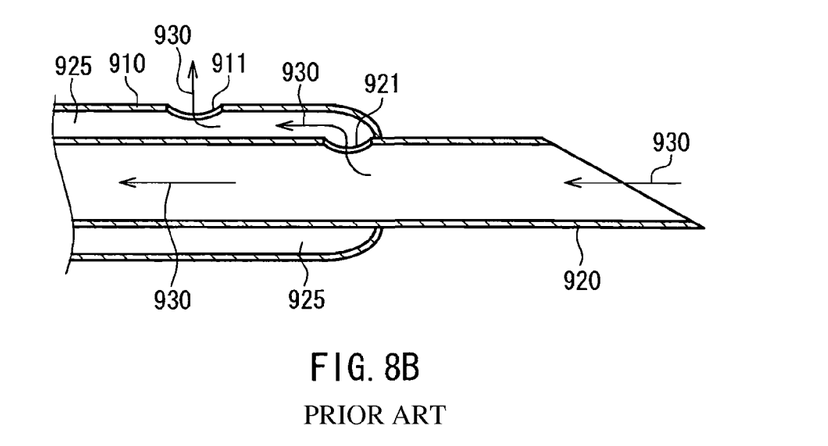
FIG. 8B is a cross-sectional view showing an imaginary indwelling needle device in which a side hole is formed in the outer needle of the indwelling needle device shown in FIG. 8A.

However, if as shown in FIG. 8B, a side hole 911 is formed in an outer circumferential face of the outer needle 910 of the indwelling needle device shown in FIG. 8A, there is a problem in that during puncture of the blood vessel of the patient, the blood 930 of the patient flowing from the inner needle 920 passes through the side hole 921 of the inner needle 920 and enters the gap 925 between the inner needle 920 and the outer needle 910, and furthermore, passes through the side hole 911 of the outer needle 910 and leaks out to the outside.

In FIG. 8B, even if the side hole 921 of the inner needle 920 is blocked, the blood of the patient flowing from the inner needle 920 passes through a hub (not shown) to which a base end (not shown) of the inner needle 920 is connected and enters the gap 925 between the inner needle 920 and the outer needle 910, and furthermore, passes through the side hole 911 of the outer needle 910 and leaks out to the outside.

The present invention has been made to solve the above-described problems, and it is an object thereof to provide an indwelling needle device in which a side hole is formed in an outer needle in order to ensure a flow channel for blood when the outer needle is left inside a blood vessel of a patient, the indwelling needle device enabling the priming operation to be performed easily by filling a gap between an inner needle and the outer needle with blood, and causing no leakage of blood through the side hole of the outer needle during puncture.

Means for Solving Problem

An indwelling needle device of the present invention includes a shield having an inner cavity, a soft outer needle fixed to a front end of the shield, a hub that is disposed within the inner cavity of the shield and is movable in a longitudinal direction of the shield, and an inner needle fixed to a front end of the hub. The hub is displaced between an initial position at which the hub is located on a front end side of the inner cavity of the shield and the inner needle penetrates the outer needle and protrudes from a leading end of the outer needle to the outside and a retracted position at which the hub is located on a rear end side of the inner cavity of the shield and the inner needle is housed within the inner cavity of the shield.

A first side hole penetrating an outer circumferential face of the outer needle is formed in the outer needle. A second side hole penetrating an outer circumferential face of the inner needle is formed in the inner needle. When the hub is in the initial position, an inner circumferential face of a region of the outer needle that contains the first side hole is in close contact with the outer circumferential face of the inner needle, and the second side hole is located closer to the hub than the region where the inner circumferential face of the outer needle is in close contact with the outer circumferential face of the inner needle.

Effects of the Invention

According to the present invention, since the first side hole is formed in the outer needle, when the outer needle is inserted into the blood vessel of the patient and left therein, even if the opening at the leading end of the outer needle is brought into contact with and blocked by the inner wall of the blood vessel, the flow channel for blood can be ensured.

Moreover, when the hub is in the initial position, the second side hole of the inner needle is located closer to the hub than the region where the inner circumferential face of the outer needle is in close contact with the outer circumferential face of the inner needle, and therefore a priming operation for filling the gap between the inner needle and the outer needle with blood easily can be performed through the second side hole.

Furthermore, when the hub is in the initial position, the inner circumferential face of the region of the outer needle that contains the first side hole is in close contact with the outer circumferential face of the inner needle, and therefore leakage of blood through the first side hole does not occur.

DESCRIPTION OF THE INVENTION

In the above-described indwelling needle device of the present invention, it is preferable that when the hub is in the initial position, a gap between the inner circumferential face of the outer needle and the outer circumferential face of the inner needle is formed in a location that is closer to the shield than the region where the inner circumferential face of the outer needle is in dose contact with the outer circumferential face of the inner needle, and the second side hole is in communication with a space between an outer face of the hub and an inner face of the shield via the gap. With this configuration, when the hub is in the initial position, the priming operation for filling with blood the space between the outer face of the hub and the inner face of the shield, in addition to the gap between the inner needle and the outer needle, easily can be performed via the second side hole.

It is preferable that when the hub is in the initial position, the first side hole is not in communication with the second side hole. With this configuration, leakage of blood through the first side hole can be prevented more reliably.

It is preferable that when the hub is in the initial position, a gap between the inner circumferential face of the outer needle and the outer circumferential face of the inner needle is formed in a location that is closer to the shield than the region where the inner circumferential face of the outer needle is in close contact with the outer circumferential face of the inner needle, and the first side hole is not in communication with the gap. With this configuration, leakage of blood in the gap between the inner needle and the outer needle through the first side hole can be prevented more reliably.

Hereinafter, the present invention will be described in detail while showing a preferred embodiment thereof. However, it goes without saying that the present invention is not limited to the embodiment below. The drawings that will be referred to in the following description show only main members of constituent members of the embodiment of the present invention that are necessary for the description of the present invention in a simplified manner for the sake of convenience of description. Accordingly, the present invention may include an optional constituent member that is not shown in the drawings below. Moreover, it should be understood that the dimensions of the members in the drawings below are not faithful representation of the dimensions of actual constituent members, dimensional ratios of those members, and the like.

Figure 1:
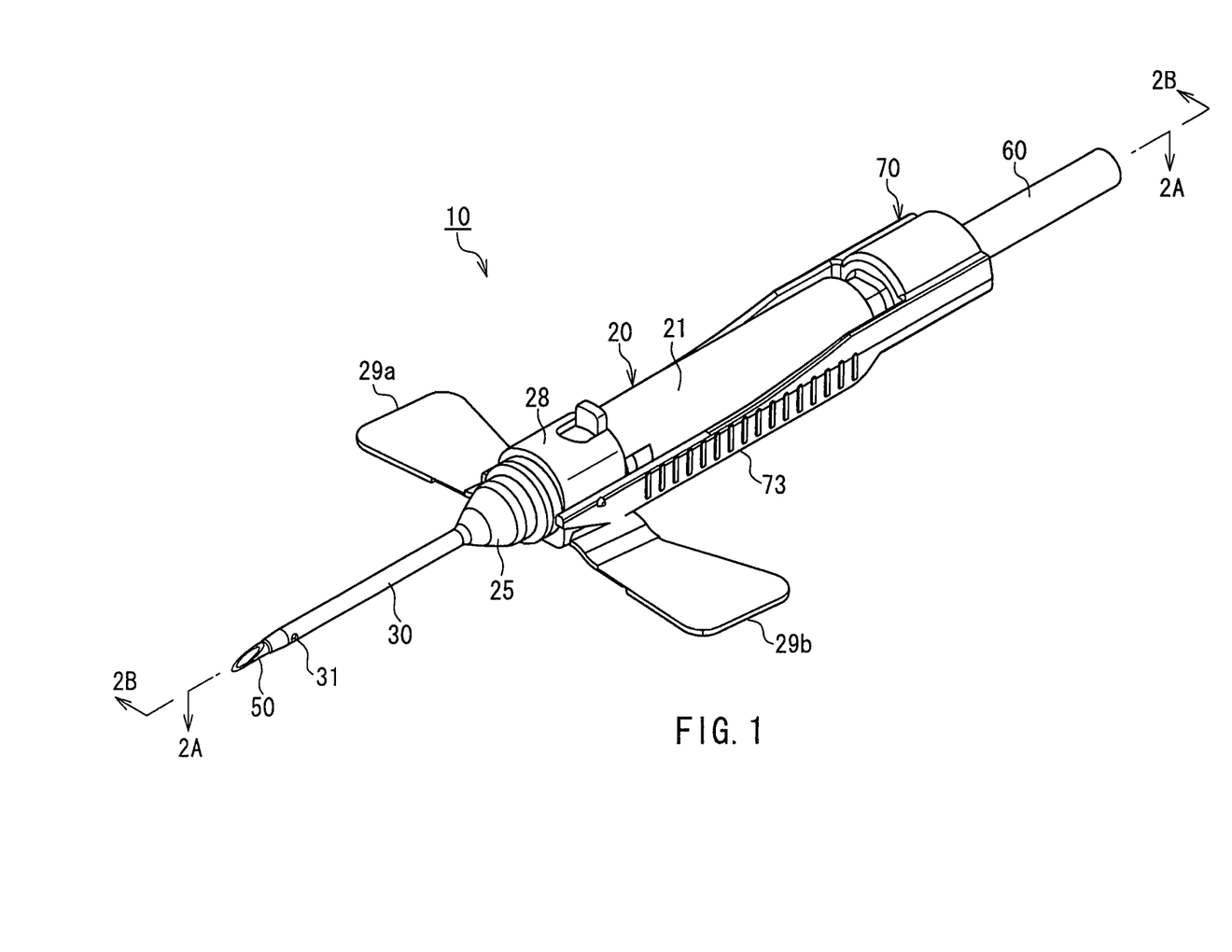
FIG. 1 is a perspective view of an indwelling needle device according to an embodiment of the present invention, with a hub being in an initial position.
Figure 2A:
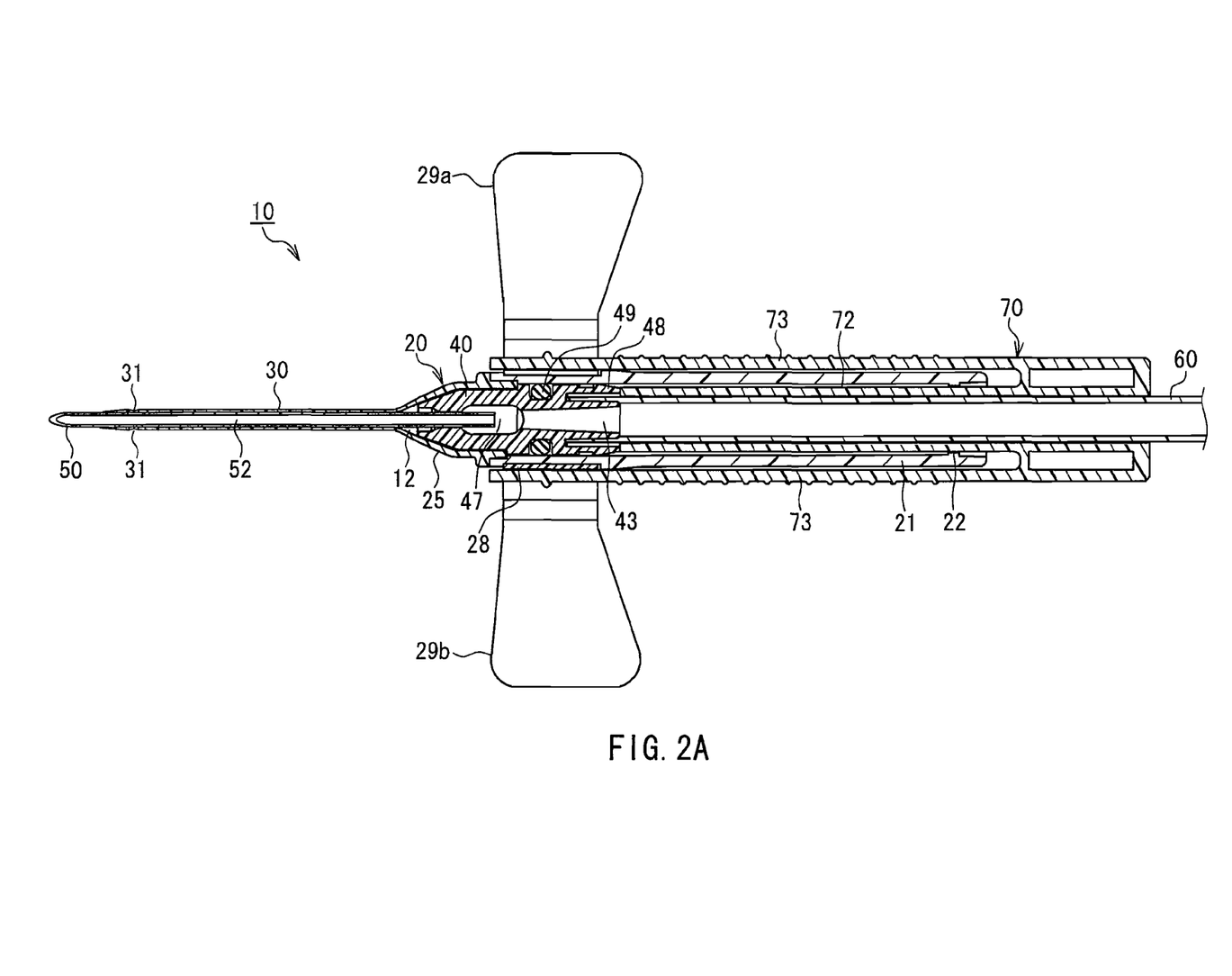
FIG. 2A is a cross-sectional plan view of the indwelling needle device according to the embodiment of the present invention taken along a plane containing line 2A-2A and seen in the direction of arrows 2A in FIG. 1.
Figure 2B:
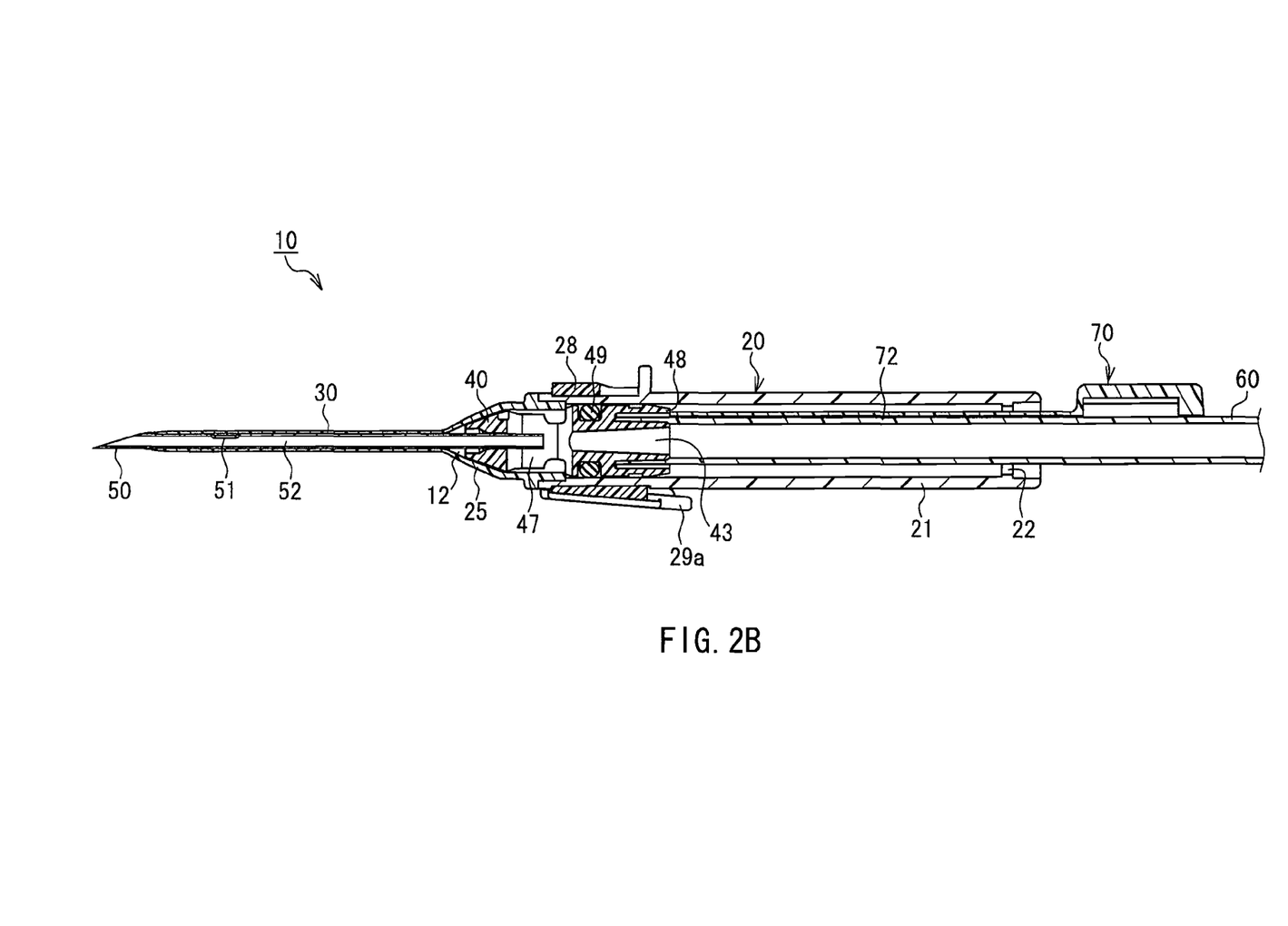
FIG. 2B is a cross-sectional side view of the indwelling needle device according to the embodiment of the present invention taken along a plane containing line 2B-2B and seen in the direction of arrows 2B in FIG. 1.

FIG. 1 is a perspective view of an indwelling needle device 10 according to an embodiment of the present invention, with a hub being in an initial position. FIG. 2A is a cross-sectional plan view of the indwelling needle device 10 taken along a plane containing line 2A-2A and seen in the direction of arrows 2A in FIG. 1, and FIG. 2B is a cross-sectional side view of the indwelling needle device 10 taken along a plane containing line 2B-2B and seen in the direction of arrows 2B in FIG. 1. In the present invention, a side that is inserted into the patient (the left-hand side on the paper plane of FIGS. 2A and 2B) is referred to as "front side", and a side that is opposite from this side is referred to as "rear side".

The indwelling needle device 10 includes a shield 20. The shield 20 has a shield tube 21 and an outer hub 25 that is fixed to an end (front end) of the shield tube 21. The shield tube 21 has an approximately cylindrical shape having a constant inner diameter. An engagement protrusion 22 that is continuous in a circumferential direction is formed in an inner circumferential face of the shield tube 21 in the vicinity of an end (rear end) that is opposite from the outer hub 25. The outer hub 25 is approximately funnel-shaped, and a soft outer needle 30 is fixed to an end (front end) thereof that is opposite from the shield tube 21. The outer needle 30 has an approximately cylindrical shape, and a pair of first side holes 31 each penetrating an outer circumferential face of the outer needle is formed in the vicinity of a leading end of the outer needle. The pair of first side holes 31 is in communication with an inner cavity of the outer needle 30. Although there is no particular limitation on the materials for the shield tube 21 and the outer hub 25, a hard material is preferable, and, for example, polycarbonate, polypropylene, and the like can be used. Preferably, the shield tube 21 and the outer hub 25 have transparency or translucency, because blood and a hub 40 inside their respective inner cavities can be seen therethrough. Although there is no particular limitation on the material for the outer needle 30, a soft material is preferable, and, for example, polypropylene, polyurethane elastomer, fluororesin such as polytetrafluoroethylene, and the like can be used. Preferably, the outer needle 30 has transparency or translucency, because blood and an inner needle 50 inside its inner cavity can be seen therethrough. It should be noted that the outer hub 25 and the outer needle 30 also may be integrally formed using the soft material described above.

Reference numerals 29a and 29b indicate wings. The wings 29a and 29b are provided on a fixing member 28 having an approximately cylindrical shape. The wings 29a and 29b are installed on the shield 20 by externally fitting the fixing member 28 to the outer circumferential face of the shield tube 21 in the vicinity of its outer hub 25 side end. Although there is no particular limitation on the material for the wings 29a and 29b, a soft material is preferable, and, for example, polypropylene, vinyl chloride, polyethylene, olefin or polystyrene thermoplastic elastomer, and the like can be used. It should be noted that the wings 29a and 29b also may be integrally formed with the shield 20.

The hub 40 is inserted in the inner cavity of the shield 20 so as to be movable in a longitudinal direction (i.e., front-rear direction) of the shield 20. The hard inner needle 50 made of metal is fixed to a front end of the hub 40, and one end of a flexible tube 60 made of resin is connected to a rear end of the hub 40. The other end of the tube 60 is connected to, for example, a blood circuit for performing hemodialysis. An O-ring 49 is installed on an outer circumferential face of the hub 40. The O-ring 49 is in close contact with the inner circumferential face of the shield tube 21 and prevents, in the inner cavity of the shield 20, blood that is present on the outer needle 30 side with respect to the O-ring 49 from leaking to the tube 60 side with respect to the O-ring 49. The inner needle 50 has an approximately cylindrical shape, and a second side hole 51 penetrating an outer circumferential face thereof is formed in the vicinity of a sharp-pointed leading end thereof. The second side hole 51 is in communication with an inner cavity 52 of the inner needle 50. Although there is no particular limitation on the material for the hub 40, a hard material is preferable, and, for example, polycarbonate, polypropylene, polyethylene, and the like can be used. Although there is no particular limitation on the material for the tube 60, a soft material is preferable, and, for example, vinyl chloride and the like can be used.

Figure 3A:
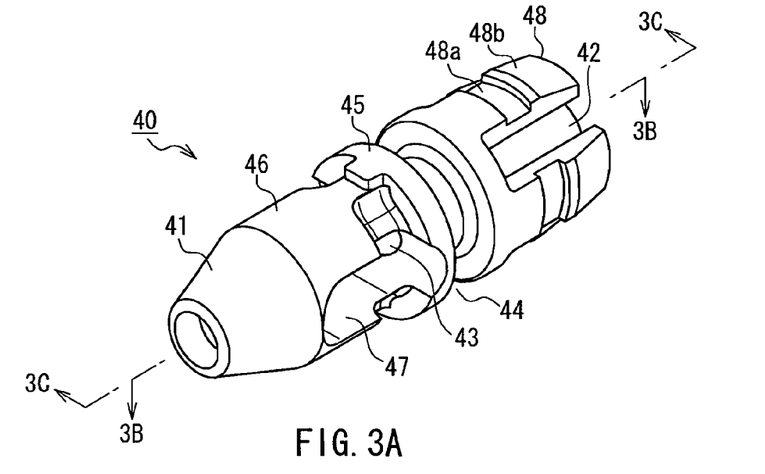
FIG. 3A is a perspective view of the hub incorporated in the indwelling needle device according to the embodiment of the present invention.
Figure 3B:
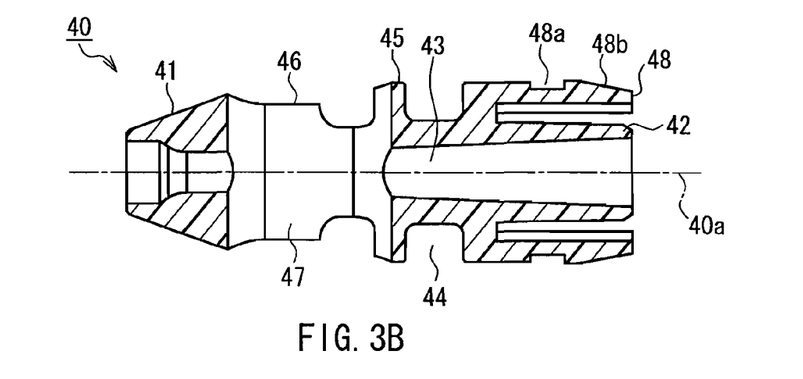
FIG. 3B is a cross-sectional plan view of the hub taken along a plane containing line 3B-3B and seen in the direction of arrows 3B in FIG. 3A.
Figure 3C:
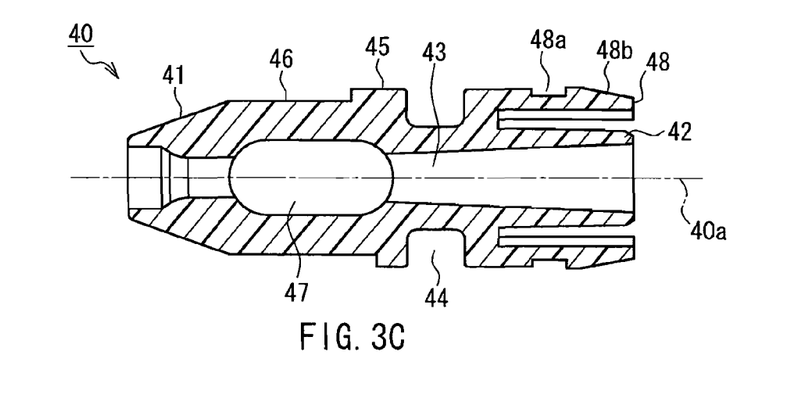
FIG. 3C is a cross-sectional side view of the hub taken along a plane containing line 3C-3C and seen in the direction of arrows 3C in FIG. 3A.

FIG. 3A is a perspective view of the hub 40, FIG. 3B is a cross-sectional plan view of the hub 40 taken along a plane containing line 3B-3B and seen in the direction of arrows 3B in FIG. 3A, and FIG. 3C is a cross-sectional side view of the hub 40 taken along a plane containing line 3C-3C and seen in the direction of arrows 3C in FIG. 3A. The hub 40 has at its one end (front end) a front portion 41 having a circular conical outer face, and has at the other end a rear portion 42 having a cylindrical outer face. A longitudinal penetration path 43 longitudinally penetrates the hub 40 and extends along a central axis 40a of the hub 40 from the front portion 41 to the rear portion 42. As shown in FIGS. 2A and 2B, the inner needle 50 is inserted into the longitudinal penetration path 43 from the front portion 41 side and held by the hub 40. The rear portion 42 is inserted into the tube 60, so that the hub 40 is connected to the tube 60. Thus, the inner needle 50 and the tube 60 are in communication with each other via the longitudinal penetration path 43 of the hub 40.

An annular groove 44 that is continuous in the circumferential direction is formed in the outer circumferential face of the hub 40 in a location between the front portion 41 and the rear portion 42. As shown in FIGS. 2A and 2B, the O-ring 49 is installed in the annular groove 44.

A large diameter portion 45 and a small diameter portion 46 are formed in the outer circumferential face of the hub 40 in respective locations between the annular groove 44 and the front portion 41, in that order from the annular groove 44 side. The small diameter portion 46 has a small outer diameter relative to the large diameter portion 45 and is adjacent to the front portion 41. A lateral penetration path 47 that laterally penetrates the small diameter portion 46 in a diameter direction (direction orthogonal to the central axis 40a) is formed in the small diameter portion 46. The lateral penetration path 47 intersects and is in communication with the longitudinal penetration path 43.

Four cantilevered elastic pieces 48 are arranged around the rear portion 42 at equiangular intervals with respect to the central axis 40a of the hub 40. The elastic pieces 48 extend approximately parallel to the central axis 40a of the hub 40. A fitting groove 48a and a tapered surface 48b are formed in a face of each elastic piece 48 that is opposite from the rear portion 42. The fitting groove 48a is a recess (groove) extending in the circumferential direction of the hub 40. The tapered surface 48b is adjacent to the fitting groove 48a on a side thereof that is closer to the free end of the elastic piece 48, and constitutes a portion of a circular conical face that has larger diameters on the fitting groove 48a side.

In FIGS. 1, 2A, and 2B, the hub 40 is located on the front end side of the inner cavity of the shield 20. In the present invention, this position of the hub 40 relative to the shield 20 is referred to as "initial position". In the initial position, the inner needle 50 held by the front portion 41 of the hub 40 penetrates the outer needle 30, and the leading end thereof is exposed to the outside from the leading end of the outer needle 30. The inner cavity 52 of the inner needle 50 is in communication with the tube 60 via the longitudinal penetration path 43 of the hub 40 and is also in communication, via the lateral penetration path 47 of the hub 40, with a space 12 between an outer face of the hub 40 that is on the front end side with respect to the O-ring 49 and an inner face of the shield 20 and a gap 13 (see FIG. 5, which will be described later) between the outer circumferential face of the inner needle 50 and the inner circumferential face of the outer needle 30.

Figure 4:
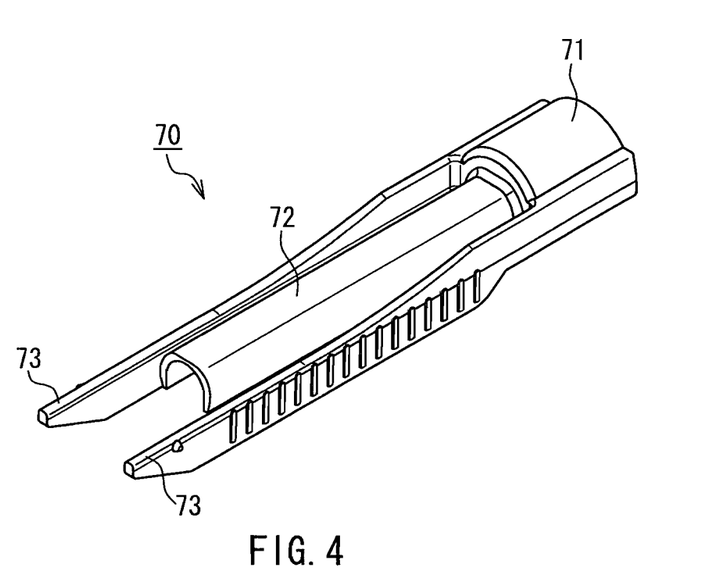
FIG. 4 is a perspective view of a stopper that is used in the indwelling needle device according to the embodiment of the present invention.

In order to maintain the hub 40 in the initial position, a stopper 70 is used. FIG. 4 is a perspective view of the stopper 70. The stopper 70 has an approximately semi-cylindrical base end portion 71, an approximately semi-cylindrical insertion portion 72, and a pair of grip portions 73. The insertion portion 72 and the pair of grip portions 73 extend upright from the base end portion 71 and parallel to one another, with the insertion portion 72 being sandwiched between the pair of grip portions 73.

As shown in FIGS. 1, 2A, and 2B, the insertion portion 72 of the stopper 70 is inserted from the rear end of the shield tube 21 into a gap between the shield tube 21 and the tube 60. When the stopper 70 is inserted into the shield 20 as far as possible, a leading end of the insertion portion 72 hits rear ends of the elastic pieces 48 of the hub 40, the large diameter portion 45 of the hub 40 in turn hits the rear end of the outer hub 25, and the hub 40 is disposed in the initial position within the inner cavity of the shield 20. At this time, the pair of grip portions 73 of the stopper 70 are located on the respective sides of the shield tube 21 of the shield 20.

Figure 5:
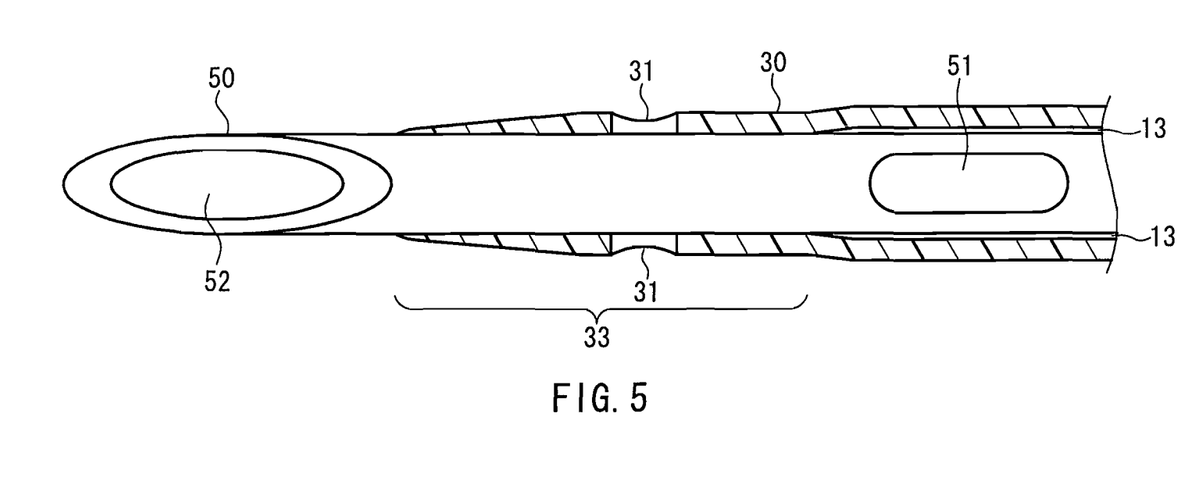
FIG. 5 is a cross-sectional view showing respective leading ends of an outer needle and an inner needle of the indwelling needle device according to the embodiment of the present invention and the vicinity thereof when the hub is in the initial position.

FIG. 5 is a cross-sectional view showing the respective leading ends of the outer needle 30 and the inner needle 50 and the vicinity thereof when the hub 40 is in the initial position. Unlike FIG. 2A, FIG. 5 shows only the outer needle 30 in cross section so that the positions of the first side holes 31 and the second side hole 51 can be seen. As shown in FIG. 5, the inner diameter of the outer needle 30 is not constant in the longitudinal direction of the outer needle 30, and the inner diameter is small in a region 33 extending a predetermined distance from the leading end of the outer needle 30 and is larger than this inner diameter on the rear side with respect to this region 33. Accordingly, in the region 33, the inner circumferential face of the outer needle 30 and the outer circumferential face of the inner needle 50 are in close contact with each other, and on the rear side with respect to the region 33, the gap 13 is formed between the inner circumferential face of the outer needle 30 and the outer circumferential face of the inner needle 50. In the present invention, the region 33 is referred to as "close contact region". The first side holes 31 are formed within the close contact region 33. Moreover, when the hub 40 is in the initial position, the second side hole 51 is located on the rear side with respect to the close contact region 33. Thus, the second side hole 51 is in communication with the gap 13. On the other hand, the first side holes 31 are in communication with neither the second side hole 51 nor the gap 13.

The manner in which the indwelling needle device 10 of the present embodiment that is configured as described above is used and the effects thereof will now be described.

As shown in FIGS. 1, 2A, and 2B, the indwelling needle device 10 with the hub 40 being in the initial position is held by sandwiching the pair of grip portions 73 of the stopper 70 between two fingers. The pair of grip portions 73 easily undergoes elastic deformation and comes into close contact with the outer circumferential face of the shield tube 21, so that the indwelling needle device 10 can be held stably. In this state, the inner needle 50 protruding from the leading end of the outer needle 30 is inserted into a blood vessel of the patient. During puncture, the inner needle 50 receives a reaction force, but since the rear end of the hub 40 (elastic pieces 48) holding the inner needle 50 abuts against the leading end of the insertion portion 72 of the stopper 70, the inner needle 50 and the hub 40 cannot be displaced relative to the shield 20.

The inner needle 50 and the outer needle 30 are inserted further inward to such an extent that the first side holes 31 of the outer needle 30 enter the blood vessel.

Insertion of the leading end of the inner needle 50 into the blood vessel causes the blood of the patient to flow into the inner cavity 52 of the inner needle 50 through the opening at the leading end of the inner needle 50. As can be understood from FIGS. 2A and 2B, the blood that has flowed into the inner cavity 52 of the inner needle 50 sequentially passes through the inner cavity 52 of the inner needle 50 and the longitudinal penetration path 43 of the hub 40 and flows into the tube 60. Moreover, the blood that has flowed into the inner cavity 52 of the inner needle 50 passes through the second side hole 51 of the inner needle 50 to flow into the gap 13 (see FIG. 5) between the inner circumferential face of the outer needle 30 and the outer circumferential face of the inner needle 50, then sequentially passes through the space 12 between the outer face of the hub 40 and the inner face of the shield 20, the lateral penetration path 47 of the hub 40, and the longitudinal penetration path 43 of the hub 40, and flows into the tube 60.

In this manner, during puncture, in addition to the inner cavity 52 of the inner needle 50, the gap 13 between the inner circumferential face of the outer needle 30 and the outer circumferential face of the inner needle 50 and the space 12 between the outer face of the hub 40 and the inner face of the shield 20 are also filled with the blood, and therefore the priming operation can be easily and quickly performed.

Moreover, since the first side holes 31 of the outer needle 30 are formed within the close contact region 33, even when the gap 13 is filled with the blood, leakage of the blood to the outside through the first side holes 31 does not occur in the process of puncture.

When the outer needle 30 and/or the shield 20 has transparency or translucency, flashback of the blood due to puncture can be visually checked.

After that, the stopper 70 is withdrawn out from the shield 20, and simultaneously or subsequently, the tube 60 is pulled from the shield 20. Since the hub 40 is connected to the front end of the tube 60, pulling the tube 60 causes the hub 40 and the inner needle 50 held by the hub 40 to move rearward relative to the shield 20.

The engagement protrusion 22 is formed in the inner circumferential face of the shield tube 21 in the vicinity of its rear end. The hub 40 moves to the engagement protrusion 22, and the tapered surfaces 48b formed in the respective outer faces of the elastic pieces 48 of the hub 40 slide on the engagement protrusion 22. At this time, the elastic pieces 48 undergo elastic deformation and deform to the rear portion 42 side. Then, when the tapered surfaces 48b have got over the engagement protrusion 22, the elastic pieces 48 undergo elastic recovery, and the engagement protrusion 22 fits in the fitting grooves 48a. The position of the hub 40 relative to the shield 20 when the fitting grooves 48a and the engagement protrusion 22 are fitted to each other is referred to as "retracted position" in the present invention.

Figure 6:
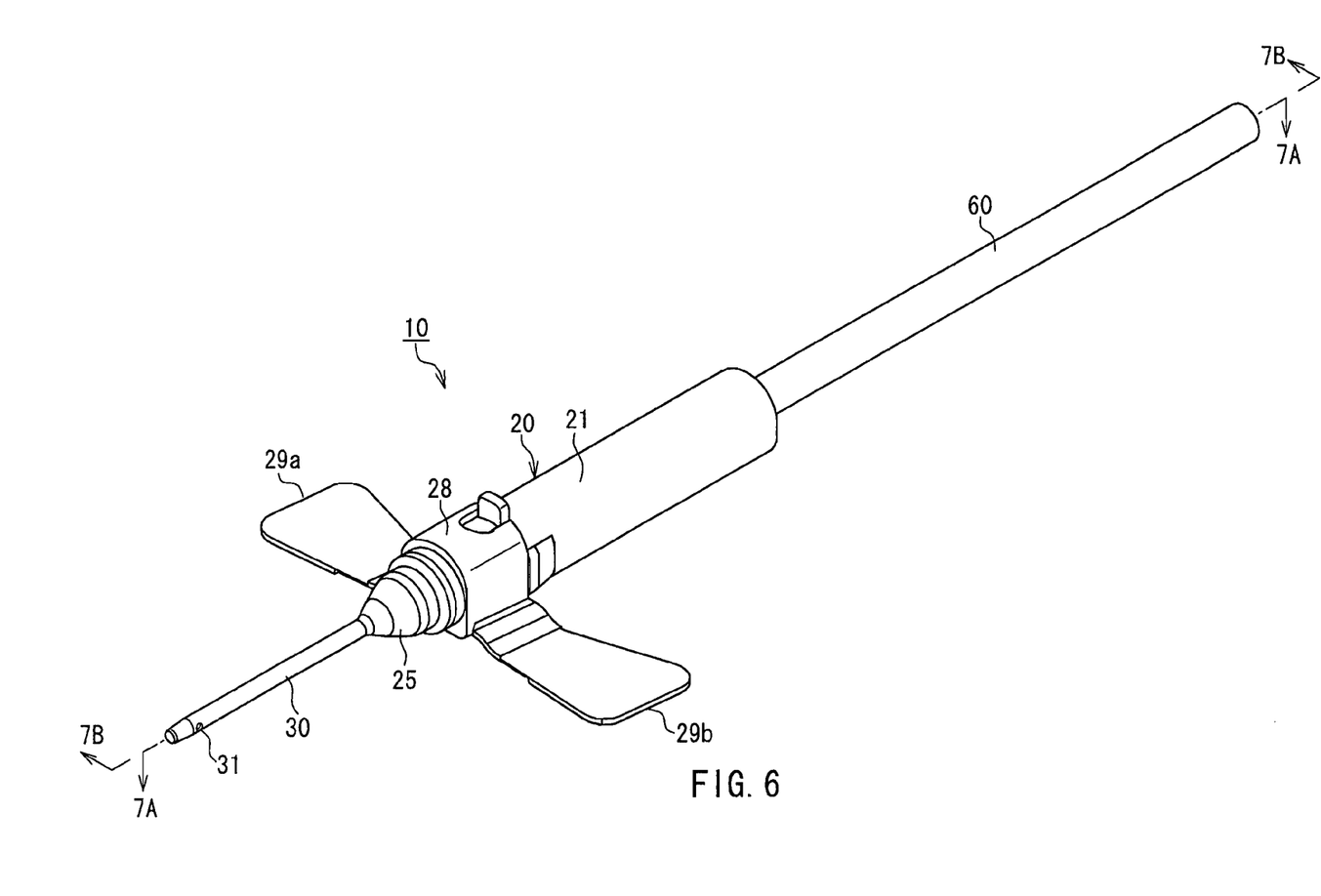
FIG. 6 is a perspective view of the indwelling needle device according to the embodiment of the present invention, with the hub being in a retracted position.
Figure 7A:
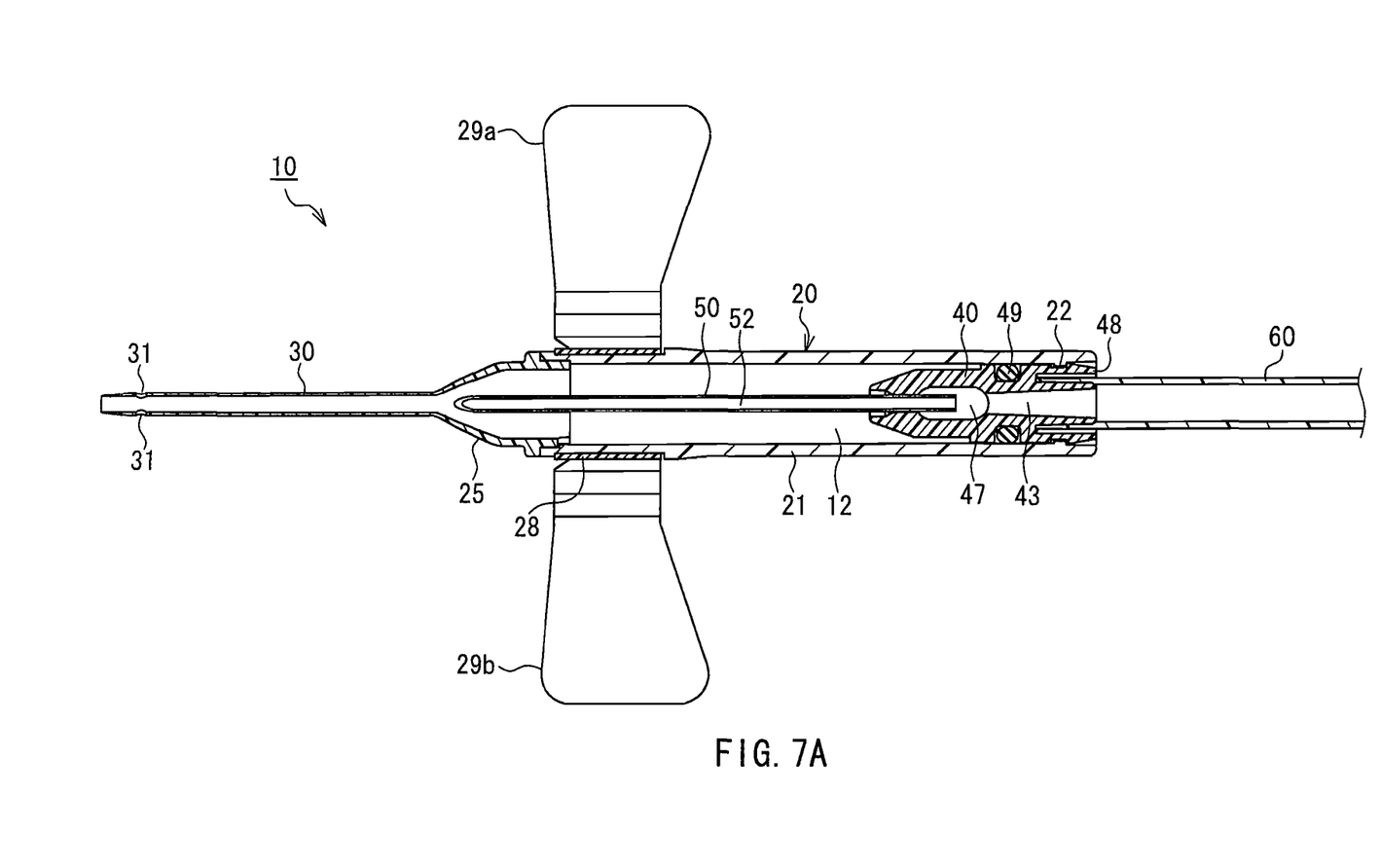
FIG. 7A is a cross-sectional plan view of the indwelling needle device according to the embodiment of the present invention taken along a plane containing line 7A-7A and seen in the direction of arrows 7A in FIG. 6.

FIG. 6 is a perspective view of the indwelling needle device 10, with the hub 40 being in the retracted position. FIG. 7A is a cross-sectional plan view of the indwelling needle device 10 taken along a plane containing line 7A-7A and seen in the direction of arrows 7A in FIG. 6, and FIG. 7B is a cross-sectional side view of the indwelling needle device 10 taken along a plane containing line 7B-7B and seen in the direction of arrows 7B in FIG. 6.

Figure 7B:
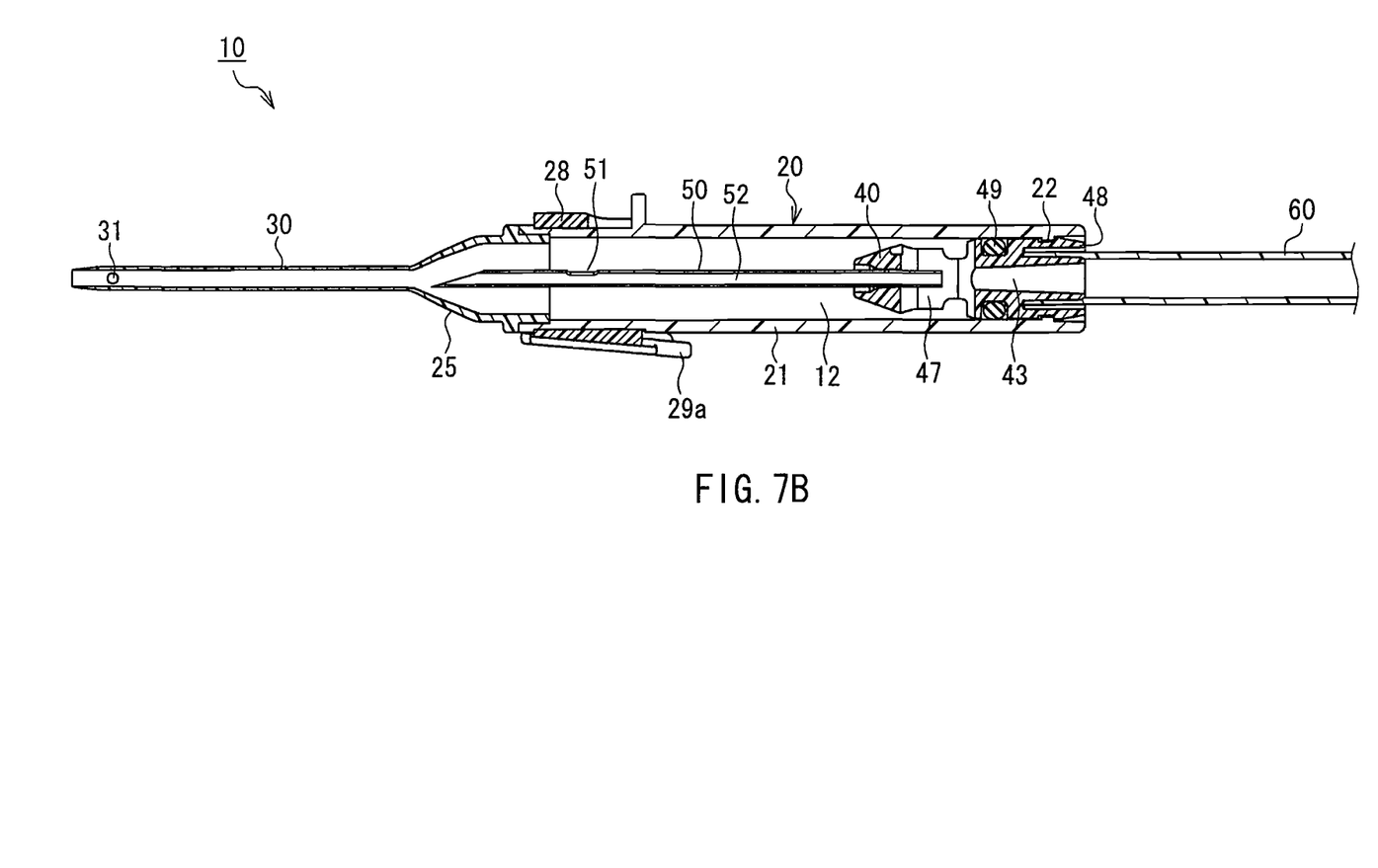
FIG. 7B is a cross-sectional side view of the indwelling needle device according to the embodiment of the present invention taken along a plane containing line 7B-7B and seen in the direction of arrows 713 in FIG. 6.

As shown in FIGS. 7A and 7B, when the hub 40 is in the retracted position, the fitting grooves 48a (see FIGS. 3A, 3B, and 3C) of the hub 40 and the engagement protrusion 22 of the shield tube 21 are fitted to each other. Moreover, the inner needle 50 held by the hub 40 has been pulled out of the outer needle 30 and is housed within the inner cavity of the shield 20.

In this state, an adhesive tape is attached to the skin of the patient over the wings 29a and 29b, and the indwelling needle device 10 thus is fixed to the patient. Only the outer needle 30 is left inside the patient in a state in which it is inserted in the patient.

When compared to the initial position (see FIGS. 1, 2A, and 2B), in the retracted position, the cross-cross sectional area of the flow channel within the outer needle 30 is increased by an amount corresponding to the cross-sectional area of the inner needle 50, and accordingly the flow rate of the blood is increased. Moreover, in the retracted position, the flow channel from the outer needle 30 to the tube 60 includes two flow channels, that is, a first flow channel sequentially passing through the inner cavity 52 of the inner needle 50 and the longitudinal penetration path 43 of the hub 40 and a second flow channel sequentially passing through the space 12 between the inner face of the shield 20 and the respective outer faces of the inner needle 50 and the hub 40, the lateral penetration path 47 of the hub 40, and the longitudinal penetration path 43 of the hub 40, and accordingly the blood can flow at a high flow rate.

In the retracted position, the hard inner needle 50 is not present in the flexible outer needle 30, and therefore, even if the position of the indwelling needle device 10 relative to the patient changes due to movement of the patient or the like, the outer needle 30 does not injure the blood vessel and the like of the patient.

Since the first side holes 31 are formed in the vicinity of the leading end of the outer needle 30, even if the opening at the leading end of the outer needle 30 is brought into contact with and blocked by the inner wall of the blood vessel, the blood can flow through the first side holes 31. Accordingly, the flow channel for the blood is ensured at all times, and a reduction in the blood flow rate can be prevented.

When the necessary treatment has been finished, the adhesive tape that fixes the wings 29a and 29b is removed from the patient, and the outer needle 30 is withdrawn from the patient. Even when the tube 60 is pushed in or pulled from the shield 20, the fitted state in which the fitting grooves 48a of the hub 40 and the engagement protrusion 22 of the shield tube 21 are fitted to each other is not released. That is to say, the inner needle 50 cannot be caused to again protrude from the leading end of the outer needle 30, and the outer needle 30 cannot be withdrawn from the shield 20 along with the hub 40. Accordingly, accidental puncture with the hard inner needle 50 and accidental reuse of the used indwelling needle device 10 are prevented. The used indwelling needle device 10 will be discarded.

The above-described embodiment should be considered as illustrative only. The present invention is not limited to the above-described embodiment, and appropriate changes can be made thereto.

For example, although two first side holes 31 were provided in the above-described embodiment, the present invention is not limited to this, and the number of first side holes also may be one or three or more. Also, there is no particular limitation regarding the shape, the dimensions, the arrangement position in the circumferential direction, and the like of the first side holes 31. However, it is necessary that the first side holes 31 are formed within the close contact region 33 and are not formed in a location that is closer to the shield 20 than the close contact region 33.

Moreover, although one second side hole 51 was provided in the above-described embodiment, the present invention is not limited to this, and the number of second side holes also may be two or more. Also, there is no particular limitation regarding the shape, the dimensions, the arrangement position in the circumferential direction, and the like of the second side hole 51. However, it is necessary that the second side hole 51 is formed in a position at which it can be in communication with the gap 13 (see FIG. 5) when the hub 40 is in the initial position. Unless the first side holes 31 are in communication with the second side hole 51 when the hub 40 is in the initial position, a portion of the second side hole 51 can be present within the close contact region 33. Considering the priming operation for filling the gap 13 between the inner needle 50 and the outer needle 30 with blood, it is preferable that when the hub 40 is in the initial position, the second side hole 51 is located in the vicinity of the close contact region 33.

As long as the hub 40 can be held in the initial position, the stopper 70 also may have a configuration other than that of the above-described embodiment. Alternatively, instead of using the stopper 70, for example, a fitting structure for fitting the hub 40 located in the initial position to the shield 20 also may be provided in the hub 40 and the shield 20.

The fitting structure for fitting the hub 40 located in the retracted position and the shield 20 to each other also may have a configuration other than the above-described configuration. Alternatively, the fitting structure may be omitted.

Although the indwelling needle device of the present invention was used for hemodialysis in the above-described embodiment, the application of the indwelling needle device of the present invention is not limited to this, and the indwelling needle device can be used for any application, such as infusion and blood transfusion, where an indwelling needle device is employed.

The embodiments described above are solely intended to illustrate the technological content of the present invention, and the present invention is not limited to or by these specific examples alone. Various modifications are possible within the scope of the claims and the spirit of the invention, and the present invention should be interpreted broadly.

INDUSTRIAL APPLICABILITY

There is no particular limitation on the field of use of the present invention, and the present invention can be extensively used as an indwelling needle device for use in treatment such as infusion, blood transfusion, extracorporeal blood circulation, and the like. Among these, the present invention can be preferably used as an indwelling needle device for hemodialysis.

REFERENCE SIGNS LIST

10 Indwelling needle device
13 Gap between outer circumferential face of inner needle and inner circumferential face of outer needle
20 Shield
21 Shield tube
25 Outer hub
30 Outer needle
31 First side hole
33 Close contact region
40 Hub
50 Inner needle
51 Second side hole
60 Tube
70 Stopper

The invention claimed is:

1. An indwelling needle device comprising:
a shield having an inner cavity;
a soft outer needle fixed to a front end of the shield;
a hub that is disposed within the inner cavity of the shield and is movable in a longitudinal direction of the shield; and
an inner needle fixed to a front end of the hub,
wherein the hub is displaced between an initial position at which the hub is located on a front end side of the inner cavity of the shield and the inner needle penetrates the outer needle and protrudes from a leading end of the outer needle to an outside and a retracted position at which the hub is located on a rear end side of the inner cavity of the shield and the inner needle is housed within the inner cavity of the shield,
a first side hole penetrating an outer circumferential face of the outer needle is formed in the outer needle,
a second side hole penetrating an outer circumferential face of the inner needle is formed in the inner needle, and
when the hub is in the initial position, an inner circumferential face of a region of the outer needle that contains the first side hole is in close contact with the outer circumferential face of the inner needle, such that the first side hole of the outer needle is blocked, and the second side hole is located closer to the hub than the region where the inner circumferential face of the outer needle is in close contact with the outer circumferential face of the inner needle.

2. The indwelling needle device according to claim 1, wherein when the hub is in the initial position, a gap between the inner circumferential face of the outer needle and the outer circumferential face of the inner needle is formed in a location that is closer to the shield than the region where the inner circumferential face of the outer needle is in close contact with the outer circumferential face of the inner needle, and the second side hole is in communication with a space between an outer face of the hub and an inner face of the shield via the gap.

3. The indwelling needle device according to claim 1, wherein when the hub is in the initial position, the first side hole is not in communication with the second side hole.

4. The indwelling needle device according to claim 1, wherein when the hub is in the initial position, a gap between the inner circumferential face of the outer needle and the outer circumferential face of the inner needle is formed in a location that is closer to the shield than the region where the inner circumferential face of the outer needle is in close contact with the outer circumferential face of the inner needle, and the first side hole is not in communication with the gap.

5. An indwelling needle device comprising:
   a shield having an inner cavity;
   a soft outer needle fixed to a front end of the shield;
   a hub that is disposed within the inner cavity of the shield and is movable in a longitudinal direction of the shield; and
   an inner needle fixed to a front end of the hub,
   wherein the hub is displaced between an initial position at which the hub is located on a front end side of the inner cavity of the shield and the inner needle penetrates the outer needle and protrudes from a leading end of the outer needle to an outside and a retracted position at which the hub is located on a rear end side of the inner cavity of the shield and the inner needle is housed within the inner cavity of the shield,
   a first side hole penetrating an outer circumferential face of the outer needle is formed in the outer needle,
   a second side hole penetrating an outer circumferential face of the inner needle is formed in the inner needle,
   when the hub is in the initial position, an inner circumferential face of a region of the outer needle that contains the first side hole is in close contact with the outer circumferential face of the inner needle, and the second side hole is located closer to the hub than the region where the inner circumferential face of the outer needle is in close contact with the outer circumferential face of the inner needle, and
   when the hub is in the initial position, a gap between the inner circumferential face of the outer needle and the outer circumferential face of the inner needle is formed in a location that is closer to the shield than the region where the inner circumferential face of the outer needle is in close contact with the outer circumferential face of the inner needle, and the second side hole is in communication with a space between an outer face of the hub and an inner face of the shield via the gap.

6. An indwelling needle device comprising:
   a shield having an inner cavity;
   a soft outer needle fixed to a front end of the shield;
   a hub that is disposed within the inner cavity of the shield and is movable in a longitudinal direction of the shield; and
   an inner needle fixed to a front end of the hub,
   wherein the hub is displaced between an initial position at which the hub is located on a front end side of the inner cavity of the shield and the inner needle penetrates the outer needle and protrudes from a leading end of the outer needle to an outside and a retracted position at which the hub is located on a rear end side of the inner cavity of the shield and the inner needle is housed within the inner cavity of the shield,
   a first side hole penetrating an outer circumferential face of the outer needle is formed in the outer needle,
   a second side hole penetrating an outer circumferential face of the inner needle is formed in the inner needle,
   when the hub is in the initial position, an inner circumferential face of a region of the outer needle that contains the first side hole is in close contact with the outer circumferential face of the inner needle, and the second side hole is located closer to the hub than the region where the inner circumferential face of the outer needle is in close contact with the outer circumferential face of the inner needle, and
   when the hub is in the initial position, a gap between the inner circumferential face of the outer needle and the outer circumferential face of the inner needle is formed in a location that is closer to the shield than the region where the inner circumferential face of the outer needle is in close contact with the outer circumferential face of the inner needle, and the first side hole is not in communication with the gap.

\* \* \* \* \*